United States Patent [19]

Schwartz et al.

[11] Patent Number: 4,680,308

[45] Date of Patent: Jul. 14, 1987

[54] STABLE SOLUBLE 1,2-DIAMINOCYCLOHEXANE PLATINUM COMPLEXES

[75] Inventors: Paul Schwartz, Rockville; Devinder S. Gill, Silver Spring, both of Md.; Kenneth J. McGrath, Mannassas, Va.

[73] Assignee: Andrulis Research Corporation, Bethesda, Md.

[21] Appl. No.: 813,451

[22] Filed: Dec. 26, 1985

[51] Int. Cl.$^4$ .................................. C07F 15/00
[52] U.S. Cl. .................................. 514/492; 556/137
[58] Field of Search ....................... 556/137; 514/492

[56] References Cited

U.S. PATENT DOCUMENTS

| | | |
|---|---|---|
| 2,166,076 | 11/1939 | Rosenblatt . |
| 4,115,418 | 9/1978 | Gale et al. ............................ 556/137 |
| 4,137,248 | 1/1979 | Gale et al. ............................ 556/137 |
| 4,200,583 | 4/1980 | Kidani et al. ..................... 556/137 X |
| 4,242,430 | 12/1980 | Hara et al. . |
| 4,560,781 | 12/1985 | Totani et al. ......................... 556/137 |
| 4,565,884 | 1/1986 | Andrulis, Jr. et al. .............. 556/137 |

OTHER PUBLICATIONS

Ridgway et al, J. Clin. Hematol. Oncol. 7 (1), pp. 220–230, (1977).

*Primary Examiner*—Helen M. S. Sneed
*Attorney, Agent, or Firm*—Millen & White

[57] ABSTRACT

Platinum complexes of the formula

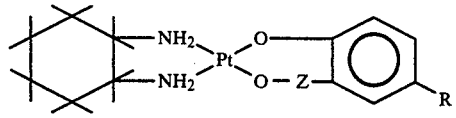

wherein Z is —CO— or a single bond and R is —COOH or —SO$_3$H, and the pharmaceutically acceptable salts thereof with bases, are stable readily water-soluble pharmaceutically active compounds having antitumor, anti-inflammatory and trypanocidal activities.

16 Claims, No Drawings

STABLE SOLUBLE 1,2-DIAMINOCYCLOHEXANE PLATINUM COMPLEXES

BACKGROUND OF THE INVENTION

This invention relates to novel 1,2-diaminocyclohexane platinum complexes having a salicylate or catecholate ligand.

Cisplatin, an approved drug for the treatment of testicular, ovarian and bladder cancers, is described in U.S. Pat. Nos. 3,892,790 and 3,904,663. Other platinum complexes which have demonstrated anti-tumor activity clinically include 1,1-dicarboxylato(diammine)-platinum(II), cis-dichloro-trans-dihydroxy-bis(isopropylamine)platinum-(IV), and 4-carboxyphthalato(1,2-diaminocyclohexane)-platinum (II). These complexes are described in U.S. Pat. Nos. 4,169,846; 4,137,248; and 4,394,319, whose disclosures are incorporated herein by reference.

Each of these prior art complexes consist of platinum bound to two amine ligands on one side of the molecule and either chloride ions or dicarboxylate ions on the other side of the molecule. This arrangement of atoms is consistent with the structure-activity relationships for active platinum complexes first defined by Cleare and Hoeschele (Bioinorganic Chemistry, 1973, 2, p. 187). To date, all reported active platinum complexes have the configuration of two inert amine ligands and two labile halide or carboxylate ligands arranged in a cis configuration. Gondolphi, et al reported the synthesis of triphenylphosphine platinum-catechol complexes which were not appreciably active (Inorganica Chim Acta, 1983, 80, p. 103).

OBJECTS OF THE INVENTION

It is an object of this invention to provide novel water soluble 1,2-diaminocyclohexane platinum complexes having substantial stability in water solutions.

Another object of the invention is to provide such complexes and pharmaceutical compositions comprising them having useful pharmaceutical activity.

A further object of this invention is to provide a method of tumor therapy employing a platinum complex of this invention.

Upon further study of the specification and appended claims, further objects and advantages of this invention will become apparent to those skilled in the art.

SUMMARY OF THE INVENTION

In a composition aspects, this invention relates to novel platinum (II) complexes of the formulae

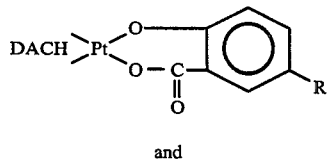

I and

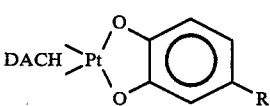

II wherein DACH = 1,2-diaminocyclohexane and R = —COOH or —SO₃H, and the pharmaceutically acceptable salts thereof with bases.

In another composition aspect, this invention relates to pharmaceutical compositions comprising one or more compounds of this invention in admixture with a pharmaceutically acceptable carrier.

In a process aspect, this invention relates to processes for the preparation and isolation of the compounds of this invention.

In another process aspect, this invention relates to methods of using the compounds of this invention as pharmaceutically active agents

DETAILED DISCUSSIONS

The complexes of this invention, in their free acid form, can be represented generically by the formula

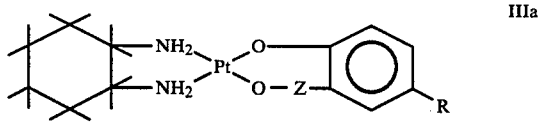

IIIa and the trans isomers thereof, by the formula

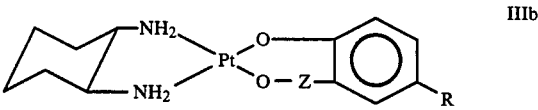

IIIb wherein in each formulae Pt is Pt(II) or Pt(IV), and R has the values given above and Z is —CO— or a single bond joining the phenolic oxygen atom to the benzene ring. In their salt form, e.g., sodium, potassium or tertiary amine, e.g., trimethylamine, trihydroxyethylamine salt, the proton of the R group is replaced by a non-toxic anion.

The compounds of this invention possess substantial pharmaceutical activities, including antiinflammatory, e.g., antiarthritic, trypanocidal and antitimor activities. For a description of platinum compounds having both trypanocidal and antitumor activities, see Farrell, N.P., Biochem Pharm., 33[1]:961-971, 1984, and of platinum compounds having antiarthritic antiinflammatory activity, see Bowen, et al, Agents and Actions, 4/2:108-112, 1974 (Birkhanser Verlag Basil).

The complexes of this invention deviate from the historical pattern for platinum complexes having antitumor activity in that the platinum phenolate linkage in the salicylate and catechol complexes is extremely stable. Althougb the resulting complexes are exceedingly stable, they retain or improve upon the antitumor activity. This solution stability allows for pharmaceutical formulations to be readily prepared as final dosage forms for clinical administration.

The platinum-salicylate complexes of this invention are the first which demonstrate substantial antitumor activity In extensive animal tumor model testing the compounds of this invention have been shown to be curative over wide dose ranges. These complexes are readily soluble and remain stable in solution over extended periods of time. These favorable physical properties combined with superior biological properties including potent antitumor activities and high therapeutic indices allow these complexes to be developed as clinically active antineoplastic drugs.

The compounds of this invention are the first platinum complexes containing salicylate or catechol ligands which possess substantial antitumor activity. Moreover, they demonstrate high levels of antitumor activity and high therapeutic indices, i.e., they have a high index of safety between toxic and therapeutically effective levels. New synthetic procedures were developed to prepare these complexes to high levels of purity. Spectroscopic and chromatographic methods were employed to determine the solution stability of these complexes. The complexes were screened against the L1210 mouse tumor model to determine antitumor activity. In addition the M5076 ovarian, B16 melanoma, and Lewis lung murine tumor models were used.

When used as antitumor agents, the platinum complexes of this invention can be administered in a manner and with a protocol comparable to Cisplatin. They advantageously are administered to patients, i.e., humans or animals, having tumors susceptable to therapeutic treatment by platinum complexes, as sterile aqueous solutions. The solutions are preferably administered intraveneously or intraarterially, although other forms of administration may be indicated in certain cases.

Solutions for intravenous injections will normally be sterile physiological solutions, which may also contain appropriate amounts of alkali, e.g., sodium bicarbonate, to convert complexes bearing acidic water-solubilizing groups to their salts. It is also possible to use pharmaceutically acceptable surfactants, e.g., naturally occurring constituents of blood which have surface active properties, e.g., salts of bile acids such as deoxycholic acid, as dispersing and/or emulsifying agents. Such natural emulsifiers have been used to disperse antibiotics, e.g., amphotericin B, in aqueous injection media. However, because the water-solubilizing R-group renders the platinum complex of the invention soluble in water, the use of such emulsifiers and/or surfactants is ordinarily not required. Suitable dosage forms can also include oily or aqueous injectable preparations, e.g., for intramuscular or intraperitoneal injection, syrups and the like liquid preparations, and solid dosage forms, e.g., capsules, tablets and the like.

The effective amounts of the complex of the invention which should be administered can be determined by conventional methods which will be apparent to the skilled clinician. Normally, the activity of the platinum complex of this invention will be evaluated in a screen along with a known complex such as Ciplatin or the (DACH)Pt(II) complexes of Gale or Kidani. The relative potency and the therapeutic index, i.e., the ratio of therapeutic effectiveness to toxicity, compared to that of the known analogue will normally determine the relative dosage compared to conventional dosages of the analogue for the type of malignancy being treated.

The treatment regimen can be varied in ways which are well known to the skilled clinician, as a function of the type of malignancy being treated, the condition of the patient, and the particular properties of the antitumor platinum complex being administered. Inevitably, a certain amount of experimentation is required to determine the optimum dosages and treatment regimens, as is normally the case for antitumor therapy.

It will sometimes be advantageous to administer the platinum complex of the invention in combination with one or more agents that potentiate its antitumor activity or mitigate undesired side effects. Such synergistic effects have been disclosed in, e.g., Gale et al., U.S. Pat. No. 4,137,248, where a platinum complex was administered with cyclophosphamide and 5-fluorouracil or hydroxyurea An antitumor effective dosage, e.g., an amount of the complex of the invention suitable for delivery of an equivalent amount of diaminoplatinum ions to the amount of such ions released by the complexes of Gale or Kidani, will generally be in the range of about 0.1–500 mg/kg/dose.

The ready solubility of the platinum complexes of this invention in water is advantageous for I.V. administration. Depending on the stability, the potency, the bioavailability and the side effects of the particular compound, oral administration may be indicated.

When used as antiinflammatory or trypanocidal agents, the compounds of this invention are preferably administered by injection, e.g., intramuscularly, in multiple doses at spaced intervals effective to achieve an antiinflammatorily or trypanocidal response in the patient suffering from an inflammatory condition or trypanocidal infection, respectively.

The Pt(II) compounds of this invention can be prepared from dichloro(1,2-diaminocyclohexane)platinum-(II), e.g., by reaction (a) with silver nitrate to produce the corresponding dinitrato compound, which is then reacted either with 5-sulfosalicylic acid or with formylsalicylic acid followed by oxidation of the formyl group of the thus-produced platinum couple to a carboxylic acid group; (b) with 3,4-dihydroxy-benzene sulfonic acid; 3,4-dihydroxy benzoic acid or 4,5-dihydroxy-1,3-benzenedisulfonic acid in presence of base. The Pt(IV) compounds of this invention can be produced from the Pt(II) compounds of this invention by mild oxidation, e.g., with a chemical equivalent amount of hydrogen peroxide.

Two synthetic approaches were employed to prepare 5-carboxysalicylato(1,2-diaminocyclohexane)platinum-(II). One involves the direct reaction of 4-hydroxyisophthalic acid with dinitrato(1,2-diaminocyclohexane)platinum, prepared from dichloro(1,2-diaminocyclohexane)platinum by reaction with silver nitrate. This synthesis requires careful manipulation of pH to obtain the proper product, i.e., the reaction must be initiated at about pH 9 and then reduced to about pH 3 to avoid the formation of undesirable byproducts.

Another procedure involves the synthesis of 5-formylsalicylato (1,2-diaminocyclohexane)platinum from formylsalicylic acid the dinitrato (DACH)platinum and subsequent oxidation of this complex with oxygen by bubbling oxygen through a THF solution of the 5-formylsalicylate complex in the presence of platinum oxide catatlyst under slightly basic conditions.

Contemplated equivalents of the compounds of this invention are those otherwise corresponding structurally thereto except they possess one or more non-interfering substituents on the cyclohexane and/or benzene rings which do not adversely affect the unique combination of stability, solubility and pharmacological activity of the basic compound, e.g., lower-alkyl, including methyl and ethyl, lower-alkoxy including methoxy and ethoxy, halo including chloro and bromo, trifluoromethyl, nitro, carboxy, sulfoxy, amido, carbamido, and ester groups, e.g., carbo-lower-alkoxy including carbethoxy, or those which possess another water-solubilizing carboxy or sulfonyloxy group acidic group on the benzene ring in addition to or instead of the R-group. Other contemplated equivalents are those otherwise corresponding structurally to Formula IIIa wherein R is another solubilizing acid group, e.g., sulfato, phosphato or carboxymethyl.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

5-Carboxysalicylato(trans-1,2-diaminocyclohexane)-platinum(II)

A. Dinitrato(trans-1,2-diaminocyclohexane)-platinum(II)

To 1.65 gm (4.3 mmole) dichloro(trans-1,2-diaminocyclohexane) platinum(II) was added 1.4 gm (8 mmole) of $AgNO_3$ and 25 ml of deionized water. This mixture was stirred in an amber bottle for 2 hours. The precipitated silver chloride was filtered off. 4-Hydroxyisophthalic acid (0.88 gms; 4.8 mmole) was dissolved in deionized water and brought to pH 9 with 5N NaOH. The platinum solution was added to the phthalic acid solution. A small amount of white precipitate formed. This was collected and the pH of the supernatant was reduced to 3 with nitric acid. The solution was kept at room temperature overnight. A pale yellow precipitate formed which was collected, washed with warm water and dried in vacuo to yield 0.95 gm of product (50%). Elemental analysis of the product gave the following results C: 32.49; H; 4.14; N: 5.40; Pt: 37.51. The calculated values are: C: 32.56; H: 4.07; N: 5.42; Pt: 37.79. Thin layer chromatography on reverse phase silica plates showed one major spot at Rf=0.8.

B. 5-Formylsalicylato(trans-1,2-diaminocyclohexane)platinum (II) This compound was prepared by the reaction of 0.47 gm (2.8 mmole) of formylsalicylic acid and 1.0 gm (2.3 mmole) of the dinitrato (DACH) platinum (II) complex in aqueous solution. The pH of the reaction mixture was 3.2. The product formed as a yellow precipitate after overnight stirring.

The resulting complex was dissolved in THF. A small amount of 1% sodium bicarbonate solution as well as a few milligrams of $PtO_2$ catalyst was added. Oxygen gas was then bubbled through the solution for a total of 48 hours. The reaction was followed by TLC which indicated the formation of a new compound. The catalyst was filtered and the solvent evaporated off to yield the product. The infrared spectrum of this product identified it as the 5-carboxysalicylate complex.

Oxidation of the thus-produced complex with 2 molar equivalents of $H_2O_2$ in water at 75° C. for 6 hours yields the corresponding Pt(IV) complex.

EXAMPLE 2

4-Carboxycatecholato(trans-1,2-diaminocyclohexane)-platinum-(II)

Dichloro(trans-1,2-diaminocyclohexane)platinum(II) (2.0 gm; 5.3 mmole) and 3,4-dihydroxybenzoic acid (0.82 gm; 5.34 mmole) were added to a 3 necked flask equipped with an argon inlet, a condenser and a pressure equilizing addition funnel. The system was thoroughly degassed and flushed with argon. Methanol, fully degassed was added to the flask with a syringe through a septum cap on the addition funnel. Potassium hydroxide (0.6 gm; 10.7 mmole) was dissolved in 110 ml of methanol and degassed and the solution was injected into the addition funnel.

The flask was heated to a gentle reflux and the KOH solution was added dropwise. The reaction mixture was further refluxed overnight. The methanol was then evaporated off and the residue was dissolved in water. The water solution was acidified with 2N acetic acid and an immediate white precipitate formed. A second precipitation yielded 1.1 gm (45%) of product. The infrared spectrum showed the presence of catecholate chelation. TLC showed one spot. Elemental analysis of the product gave the following results: C: 31.4; H: 4.20; N: 5.59; Pt: 39.2. The calculated values for the title compound are C: 31.38; H: 4.42; N: 5.63; Pt: 39.22.

Oxidation of the thus-produced complex with $H_2O_2$ as described in Example 1 yields the corresponding Pt(IV) complex.

Similarly, 4-sulfocatecholato(1,2-diaminocyclohexane)-platinum (II) is prepared by substituting 3,4-dihydroxy-benzenesulfonic acid for the 3,4-dihydroxybenzoic acid.

EXAMPLE 3

5-Sulfosalicylato(trans-1,2-diaminocyclohexane) platinum(II)

Dichloro(1,2-diaminocyclohexane)platinum(II) was prepared using the pure trans diaminocyclohexane isomer which was separated from the cis- trans mixture by the method of Kidani (U.S. Pat. No. 4,169,846). Silver nitrate (0.87 gm; 5.1 mmole) was added to 30 ml of deionized, water and then 1.0 gm (2.6 mmole) of the pure dichloro(trans-1,2-diaminocyclohexane) platinum complex was added to the solution. The mixture, protected from the light with aluminum foil, was stirred at room temperature overnight.

The silver chloride which had precipitated was filtered off on a fine sintered glass funnel and the supernatant, containing dinitrato(1,2-diaminocyclohexane)-platinum(II) dissolved therein, was added dropwise to a water solution of 5-sulfosalicylic acid (0.65 gm; 2.6 mmole).

A small amount of precipitate formed which was filtered off. The pH of the filtrate was raised to 9 with 1N NaOH and the solution of the thus-produced sodium salt of the title compound, was stirred at room temperature overnight. The solution was filtered and the filtrate was acidified with dilute nitric acid to a pH of 1.5. A white precipitate formed which was filtered, washed with water and dried under vacuum to give 0.73 gm of product (51%).

Elemental analysis of the product gave the following results: C: 27.92; H: 4.01; N: 5.27; S: 5.69; Pt: 34.69. The calculated values for the title compounds are: C: 27.81; H: 3.95; N: 4.99; S: 5.71; Pt: 34.75.

Oxidation of the thus-produced complex with $H_2O_2$ as described in Example 1 yields the corresponding Pt(IV) complex.

Similarly, the corresponding cis- complexes are produced by substituting cis-1,2-diaminocyclohexane for the trans-isomer thereof as starting material.

The following illustrates the preparation of an analogue of the compounds of this invention having two rather than one acid groups on the benzene ring. 3,5-Disulfocatecholato(trans-1,2-diaminocyclohexane)-platinum (II)

This complex was formed by the reaction of Tiron (4,5-dihydroxy-1,3-benzene disulfonic acid, disodium salt) and the dichloro(trans-1,2-diaminocyclohexane)-platinum(II) complex in methanol under strictly inert atmosphere conditions. These conditions must be rigidly observed to prevent oxidation of the catechol and reduction of the platinum to platinum metal in the presence of methanolic KOH. The reaction mixture was heated under mild reflux for several hours. After cooling and filtering off any unreacted insoluble material, the methanol was evaporated off. The residue was redissolved in water and the pH reduced to 1 with nitric acid. The water solution was evaporated to dryness to give a light orange product in 50% yield. Infrared analysis of the product showed it to be the platinum sulfocatechol complex.

Oxidation of the thus-produced complex with $H_2O_2$ as described in Example 1 yields the corresponding Pt(IV) complex.

In addition to the above compounds, other complexes with catechol or salicylate ligands can be prepared by the same reactions. For example, each of the above Pt(II) complexes can be easily oxidized to form the corresponding Pt(IV) complexes.

Stability Studies

An essential element of this invention is the ready solubility and the enhanced stability of the new compared to previously prepared platinum complexes with antitumor activity. These features allow these complexes to be easily formulated as intravenous injectables for clinical use.

As an example, the compound 4-carboxyphthalato(1,2-diaminocyclohexane) platinum, which is described in U.S. Pat. No. 4,137,248, was very active in animal tumor screens and has shown some clinical efficacy (Dev. Oncol., 17, p. 310, 1984). The compound has not been developed as a drug because of its instability in solution, which can be demonstrated by the ultraviolet spectra of the complex in solution run at half-hour intervals. The decrease in absorbance with time is a measure of complex decomposition The half-life for decomposition of the prior art compound is approximately 2 hours whereas the identical experiment performed on the carboxysalicylate complex of this invention shows that the complexes of this invention are approximately 20 times more stable. This improved stability is a unique feature of the compounds of this invention.

Antitumor Properties

The compounds of this invention were tested for antitumor effects using the L1210 murine tumor model In a typical experiment 100,000 tumor cells were injected into BDF1 mice. On days 1, 5 and 9 after the cell innoculum, the mice were treated by injection with solutions of the compounds. The results of the experiments were evaluated on day 30 and are expressed as the median day of death of the treated mice divided by the median day of death of the untreated control mice (T/C%). Mice with no sign of tumor on day 30 are considered as cured. The results of these experiments are presented in the following table.

| Platinum Complex | Dose (mg/kg) | T/C % | Cures |
|---|---|---|---|
| 5-Carboxy-salicylate | 3.12 | 166 | 0 |
|  | 6.25 | 333 | 2/6 |
|  | 12.5 | 333 | 4/6 |

| Platinum Complex | Dose (mg/kg) | T/C % | Cures |
|---|---|---|---|
|  | 25 | 233 | 2/6 |
| 4-Carboxy-catechol | 25 | 128 | 0 |
|  | 50 | 134 | 0 |
|  | 100 | 357 | 3/6 |
|  | 200 | 357 | 4/6 |
| 5-Sulfo-salicylate | 1.56 | 147 | 0 |
|  | 3.12 | 340 | 6/6 |
|  | 6.25 | 340 | 4/6 |
|  | 12.5 | 340 | 5/6 |
|  | 25 | 340 | 3/6 |

As can be seen, these new compounds are highly active over wide dose ranges. This features offers additional clinical advantages in that the physician can treat patients at doses which are effective at much lower than toxic doses. This margin of safety known as a therapeutic index (TI) is defined as a ratio of toxic to effective doses. The compounds of this invention exhibit much larger TI's than Cisplatin, the currenty used platinum anticancer drug.

In addition to the L1210 tumor line, the sulfosalicylate complex was screened against additional murine tumor models. In these experiments, tumor of a known weight was implanted subcutaneously to the mice. The mice were then treated with the compound on a day 1, 5, 9 schedule. On day 30, the tumors were reweighed and the results are expressed as per cent inhibition of tumor weight.

| Tumor | Dose | % Inh. |
|---|---|---|
| B-16 melanoma | 3 | 24 |
|  | 6 | 52 |
|  | .12 | 60 |
| Lewis Lung Carcinoma | 3 | 29 |
|  | 6 | 25 |
|  | 12 | 62 |
| M-5 Ovarian Carcinoma | 3 | 71 |
|  | 6 | 93 |
|  | 12 | 99 |
| X5563 Plasma Cell Myeloma | 3 | 100 |
|  | 6 | 100 |
|  | 12 | 100 |

Activity against these various types of cancers further substantiates the clinical activity of the compounds of this invention.

The preceding examples can be repeated with similar success by substituting the generically or specifically described reactants and/or operating conditions of this invention for those used in the preceding examples From the foregoing description, one skilled in the art can easily ascertain the essential characteristics of this invention, and without departing from the spirit and scope thereof, can make various changes and modifications of the invention to adapt it to various usages and conditions.

WHAT IS CLAIMED IS:

1. A platinum complex of the formula

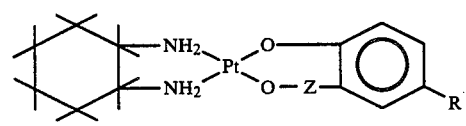

wherein Z is —CO— or a single bond and R is —COOH or —SO₃H, or a pharmaceutically acceptable salt thereof.

2. A complex according to claim 1, wherein Pt is Pt(II).

3. A complex according to claim 1, wherein the cyclohexane ring is in the trans configuration.

4. A complex according to claim 1, wherein Z is a single bond.

5. A complex according to claim 1, wherein Z is —CO.

6. A complex according to claim 1, wherein R is —COOH.

7. A complex according to claim 1, wherein R is —SO₃H.

8. 4-Carboxycatecholato(trans-1,2-diaminocyclohexane) -platinum(II), a complex according to claim 1.

9. 5-Sulfosalicylato(trans-1,2-diaminocyclohexane) -platinum(II), a complex according to claim 1.

10. 5-Carboxysalicylato(trans-1,2-diaminocyclohexane) -platinum(II), a complex according to claim 1.

11. 4-Sulfocatecholato(trans-1,2-diaminocyclohexane) -platinum(II), a complex according to claim 1.

12. A pharmaceutical composition comprising a concentration effective to achieve an antitumor effect against a tumor respsonsive to platinum complex antitumor therapy, of a complex according to claim 1 in sterile admixture with a pharmaceutically acceptable carrier adapted for systemic admistration.

13. An admixture according to claim 12, adapted for intravenous administration.

14. An admixture according to claim 12, wherein the vehicle is aqueous.

15. An admixture according to claim 12, wherein the complex is 5-sulfosalicylato(1,2-diaminocyclohexane)-platinum (II).

16. An admixture according to claim 12, wherein the complex is 5-carboxysalicylato(1,2-diaminocyclohexane)platinum (II).

* * * * *